United States Patent [19]

Magistro

[11] Patent Number: 5,087,791
[45] Date of Patent: Feb. 11, 1992

[54] PROCESS FOR THE PREPARATION OF ETHYLENE AND VINYL CHLORIDE FROM ETHANE IN THE PRESENCE OF WATER

[75] Inventor: Angelo J. Magistro, Bricksville, Ohio

[73] Assignee: The B. F. Goodrich Company, Brecksville, Ohio

[21] Appl. No.: 615,193

[22] Filed: Nov. 19, 1990

[51] Int. Cl.⁵ ............................................. C07C 5/327
[52] U.S. Cl. ..................................... 585/657; 585/658
[58] Field of Search ................................ 585/657, 658

[56] References Cited

U.S. PATENT DOCUMENTS 4,102,935  7/1978  Kroenke et al. .................. 585/658
4,102,936  7/1978  Magistro .......................... 585/658

Primary Examiner—Patrick P. Garvin
Assistant Examiner—E. D. Irzinski
Attorney, Agent, or Firm—Joe A. Powell

[57] ABSTRACT

Ethylene is prepared in an oxydehydrogenation reaction of ethane by contacting a charge amount of ethane, an oxygen source, a chlorine source and water in the presence of a solid solution catalyst at an effective temperature. A low yield of vinyl chloride and a high yield of ethylene are obtained at a high ethane conversion.

13 Claims, No Drawings

PROCESS FOR THE PREPARATION OF ETHYLENE AND VINYL CHLORIDE FROM ETHANE IN THE PRESENCE OF WATER

This invention relates to the preparation of ethylene and the subsequent preparation of vinyl chloride monomer from ethane using water as an additive.

BACKGROUND OF THE INVENTION

A widely used method for making vinyl chloride monomer is the oxychlorination of ethylene to form ethylene dichloride which is subsequently dehydrohalogenated to form the vinyl chloride monomer. In the oxychlorination of ethylene, an oxygen source and hydrogen chloride are contacted with ethylene in the presence of a suitable catalyst.

Due to the relatively high price of ethylene versus ethane, processes for the preparation of vinyl chloride from ethane have been developed. One method comprises contacting ethane, an oxygen source and a chlorine source in the presence of a catalyst. The catalyst is typically a transition metal compound, such as cupric chloride or iron oxide, supported on a support structure or material, such as aluminum oxide. In addition to vinyl chloride monomer, ethylene is a reaction product. In refining this process, efforts have focused on maximizing the yield of vinyl chloride. British Patent Specification No. 1,039,369 discloses such a process in which water is used as an additional reagent, and that high yields of vinyl chloride can be obtained. The water is used to control the heat of the reaction, and since high levels of hydrogen chloride are added to maximize the yield of vinyl chloride, the water also preserves the iron oxide catalyst by preventing its conversion to iron chloride. The ethylene is separated from the vinyl chloride monomer and is recovered to be used in other processes. This process has two disadvantages. First, the separation of vinyl chloride from ethylene is a complex and costly step, and second, the yield of vinyl chloride per mole of ethane reagent is relatively low, typically less than 50%.

Therefore, it is desired to have a process for preparing ethylene from ethane wherein relatively small amounts of vinyl chloride are formed, and the conversion of ethane to ethylene is high. This ethylene prepared from ethane could then be fed directly to an oxychlorination reaction to be converted to ethylene dichloride, which could then be directly processed to vinyl chloride.

SUMMARY OF THE INVENTION

This invention is a process for preparing ethylene from ethane, comprising contacting a charge amount of ethane, an oxygen source, a balanced amount of a chlorine source relative to the amount of ethane, and water in the presence of a solid solution catalyst containing iron cations stabilized with a metal oxide stabilizer, at an effective temperature. The process forms less than 6.0% by weight of vinyl chloride monomer and greater than 75% ethylene as reaction products at at least an 80% conversion of ethane.

In another aspect, this invention is a process for preparing ethylene dichloride comprising contacting the reaction product formed from the above process with a chlorine source in the presence of a suitable catalyst at an effective reaction temperature.

In yet another aspect, this invention is a process for preparing vinyl chloride monomer comprising dehydrohalogenating the reaction product formed in the above-described process.

By adding water in the initial reaction step, the formation of vinyl chloride monomer is reduced compared to a reaction of the same reactants, catalyst and conditions but in the absence of water. Thus, the reaction product can be directly fed to an oxychlorination reaction to prepare ethylene dichloride which can then be fed directly to another reaction site and processed to vinyl chloride monomer. The need for removing the vinyl chloride monomer from the first oxychlorination reaction product is avoided.

DETAILED DESCRIPTION OF THE INVENTION

Although the primary aspect of this invention is the preparation of ethylene from ethane in the presence of water, in the aspect of this invention of preparing vinyl chloride from ethane in at least three successive steps, these steps shall be referred to as an oxydehydrogenation (i.e. the oxydehydrogenation of ethane to ethylene); an oxychlorination (i.e. the oxychlorination of ethylene to ethylene dichloride); and a dehydrohalogenation (i.e. the dehydrohalogenation of ethylene dichloride to vinyl chloride).

The reactants of the process of this invention are ethane, an oxygen source, a chlorine source and water. The amounts of the reactants added in the process will be referred to relative to a charge amount of ethane (i.e. the amount of ethane will be the base amount). The chlorine source is preferably hydrogen chloride gas. A balanced amount of the chlorine source relative to the amount of ethane is employed. Such amount is no more than an amount which ideally would yield one mole of ethylene dichloride per mole of ethane initially charged to the reaction medium without the formation of any hydrogen chloride or vinyl chloride as byproducts. Thus, for hydrogen chloride as the chlorine source, no more than two moles of hydrogen chloride are added for each mole of ethane. Alternatively, if chlorine gas, $Cl_2$, is used, then no more than one mole of chlorine gas per mole of ethane is added. Using this limited amount of chlorine source will result in lower yields of hydrogen chloride and vinyl chloride sideproducts. Since the conditions are not perfect and the process not totally efficient, preferably less than two moles of the hydrogen chloride or the equivalent amount of a different chlorine source is employed. Using such a reduced amount will result in lower sideproducts yields, but it will also result in lower ethane conversion. Advantageous results of a balance between a low amount of sideproduct formation and high ethane conversion can be obtained if the hydrogen chloride is added at an amount of between about 0.7 moles to about 1.8 moles, preferably between about 1.4 to about 1.75 moles per mole of ethane.

Oxygen can be added in a variety of forms, including pure oxygen, i.e., $O_2$, or in the form of air. Since water is another reactant, moist air is suitable as well as dry air. The oxygen is added to convert the ethane to ethylene and to yield water as a sideproduct. For a given amount of chlorine source added, a greater amount of oxygen added will generally result in a higher ethane conversion but a lower selectivity to ethylene and a higher selectivity to vinyl chloride. In a completely efficient reaction, a half a mole of oxygen per mole of ethane will be added to yield a mole of ethylene. Yet, the reaction is less than efficient, and so the amount of oxygen added is between about 0.35 to about 0.7, and preferably between about 0.4 to about 0.65 mole per mole of ethane.

Water is added along with the ethane, oxygen source and chlorine source. Since the reaction is conducted at temperatures greater than the vaporization temperature of water, the water can be added as steam along with the other gaseous reactants. For a given amount of chlorine and oxygen added, a greater amount of water will yield a lower ethane conversion but a higher selectivity to ethylene and a lower selectivity to vinyl chloride. Thus, any amount of water will be suitable depending on the desired results. However, adding very high amounts of water is commercially impractical since the water dilutes the reaction stream. Thus, to obtain the desired ethane conversion and ethylene selectivity, a very large reactor will be required. A desirable balance between ethane conversion and selectivity to ethylene is found when the amount of water added is between about 0.5 to about 3.0, and preferably from about 0.7 to about 1.5 moles per mole of ethane.

The temperature of the reaction ranges between about 400° C. to about 650° C., preferably between about 475° C. to about 600° C. Generally the higher the reaction temperature the higher the ethane conversion.

The catalyst used in the process of this invention is a solid solution catalyst. Suitable catalysts are disclosed and described in U.S. Pat. Nos. 4,102,935, 4,102,936, 4,158,645 and 4,159,968, herein incorporated by reference.

The solid solution catalysts useful in this invention contain iron cations substituted for cations in a host lattice and are stabilized with a metal oxide stabilizer. These solid solution catalysts are in contrast to catalysts wherein an active ingredient such as cupric chloride or iron oxide is merely adsorbed onto the surface of a support structure or material. The difference is crucial and can be distinguished both in the physical state of the catalyst and in the activity of the catalyst.

The solid solution catalyst is a true solution wherein iron cations are substituted for host lattice ions in the catalyst structure. An x-ray diffraction pattern of a solid solution catalyst is characteristic of the diffraction pattern of the host lattice. For example, a solid solution catalyst of $Fe_2O_3$ in $\alpha$-$Al_2O_3$ will exhibit an x-ray diffraction pattern characteristic of $\alpha$-$Al_2O_3$. In contrast, if $Fe_2O_3$ is merely adsorbed onto $\alpha$-$Al_2O_3$, the x-ray diffraction pattern will show the presence of both $Fe_2O_3$ and $\alpha$-$Al_2O_3$.

A distinguishing feature of the solid solution catalysts useful in this invention, i.e., solid solution catalysts containing iron and stabilized with a metal oxide stabilizer, is in the increased retention of iron upon use. For example, an $\alpha$-$Al_2O_3$ solid solution catalyst containing iron cations and stabilized with lanthanum cations used at reaction conditions of 1 mole ethane/0.6 mole oxygen/1.5 mole hydrogen chloride lost about 3% by weight of its original iron content after about 100 hours of use. Also, a catalyst which is a simple solid solution of iron in $\alpha$-$Al_2O_3$ lost about 4% by weight of its iron content under the same conditions. In contrast, a catalyst comprised of ferric oxide merely adsorbed onto $Al_2O_3$, operating under the same set of conditions, lost over 8% by weight of its original iron content after about 100 hours of use.

The iron cations in solid solution catalysts can be of different types. The iron can exist as ferric ($Fe^{+3}$) and/or ferrous ($Fe^{+2}$) ions. The ferric ion is the active ion in the catalyst. However, as the ferrous ion can oxidize to a ferric ion in the process, the use of solid solution catalysts containing ferrous ions are within the scope of the invention.

In the solid solution catalyst containing iron cations there is direct substitution of iron ions for host lattice ions. An example of this catalyst is $(Fe_x^{+3}M_{2-x}^{+3})O_3$ wherein x is greater than 0 and less than 2 and M is a metal such as Al or Cr. An example of this is a solid solution catalyst of ferric oxide ($Fe_2O_3$) in aluminum oxide ($Al_2O_3$). As the ferric ion is much greater in size than an aluminum +3 ion, the solubility of the ferric ion in aluminum oxide is limited. For the solid solution catalysts in which M is aluminum, x has an upper limit of about 0.15. The most preferred host lattice is attrition resistant $\alpha$-$Al_2O_3$ prepared by calcining $\delta$-alumina as is disclosed in copending U.S. patent application Ser. No. 07/402,909, filed Sept. 12, 1989.

The preferred $\alpha$-alumina catalyst support or host lattice useful in this invention can be prepared from $\delta$-alumina precursors available from Ketjen, a subsidiary of Akzo Chemical BV, Amersfoort, The Netherlands, by any convenient method known in the art for preparing $\alpha$-alumina from $\delta$ or other alumina precursors. In one suitable method to convert the precursor alumina to the $\alpha$-phase, the precursor material is heated to at least about 1150° C. Temperatures lower than about 1150° C. do not result in substantial conversion of the precursor alumina to the $\alpha$-alumina phase. While temperatures to about 1700° C. or higher may be employed, it should be noted that the $\alpha$-alumina obtained at higher temperatures have lower surface areas. The conversion is preferably carried out between about 1150° C. and 1300° C., and most preferably at about 1250° C. A calcination time of about 4 to 24 hours is suitable to obtain substantially complete conversion to $\alpha$-alumina, although shorter or longer times (contingent upon temperature) may be employed without detriment to the support. The calcination may be effected in any calcination apparatus known in the art. Non-limiting examples include ovens, muffle furnaces or tunnel furnaces containing fixed beds or moving beds, rotary kilns, and the like.

The surface area of the resulting $\alpha$-alumina is between about 0.1 to 14 $m^2/g$, preferably from about 3 to 10 $m^2/g$, and most preferably from about 5 to 7 $m^2/g$. The desired surface area can be arrived at by controlling the calcining conditions (e.g., time and temperature).

A special advantage of these attrition resistant, $\alpha$-alumina catalyst supports or host lattices is that the surface areas of the support particles are relatively stable to changes in temperature and chemical environment. This is advantageous in high temperature catalytic processes in eliminating fluctuating reaction efficiencies due to changes in the surface area of the support material. Accordingly, the $\alpha$-alumina catalyst supports or host lattices are particularly useful in a variety of high temperature catalytic processes (e.g., between about 500° C. to about 1000° C.), but can also be utilized at lower temperatures where a high attrition support might be useful.

The solid solution catalysts containing iron are stabilized with a metal oxide stabilizer. The metal oxide increases the useful life of the solid solution catalyst compared to a catalyst without such stabilizers, and also assists in lowering the yield of vinyl chloride. Although the metal oxide is an integral part of the catalyst, it is believed that the metal oxide does not enter into solid solution with the host lattice as does the iron.

The metal oxide stabilizer can be employed in the solid solution singly or as mixtures of the metals. Generally, the metals are large size atoms with a valence of +2 or +3. Examples of the metals are lanthanides, i.e., elements 50 to 71 of the Periodic Table. The preferred lanthanides used are Lanthanum, Cerium, Praseodymium, Neodymium, and Erbium. Other preferred metals include chromium, barium, manganese and cobalt. A preferred catalyst consists of a solid solution catalyst containing iron and stabilized with lanthanum, praseodymium or neodymium. Excellent results have been obtained using a catalyst of $Fe_2O_3$ in $\alpha$-$Al_2O_3$ stabilized with lanthanum.

The solid solution catalysts useful in this invention contain iron but have x-ray diffraction patterns characteristic of the host lattice material. Solid solutions are known to exist (see C. S. Barrett, *Structure of Metals, Crystallographic Methods, Principles, and Data*, 2nd Ed., McGraw-Hill Book Co., Inc., NY, N.Y. (1952), at pages 220 et seq.).

The catalyst can be identified and characterized by analyzing it to determine what elements it contains. This can be done using techniques such as chemical analysis, atomic absorption spectroscopy, x-ray fluorescence spectroscopy, and optical microscopy. For example, analysis by wet chemical analysis and x-ray fluorescence of the solid solution catalyst of iron oxide in aluminum oxide, stabilized with lanthanum would show iron, lanthanum, aluminum, and oxygen to be present in the catalyst. The presence and quantity of iron in the catalyst can be readily determined using a standard method of chemical analysis such as the dichromate method for the determination of iron. The amount of iron in the solid solution catalysts is limited by the solubility of the ions in the host lattice. Thus, the amount of iron in the catalyst will vary according to the type of host lattice used. The solid solution catalysts can contain from about 0.1 percent to 20 percent by weight and more preferably from about 0.5 percent to about 10 percent by weight of iron in the catalyst expressed as iron oxide. The catalyst can contain a similar level of the metal oxide stabilizer. To further identify and characterize the catalyst, an x-ray diffraction scan is run on the catalyst. The x-ray diffraction scan will show a pattern of peaks, which peaks have positions and intensities distinctive of the crystalline phases which are present. The x-ray diffraction peak positions and intensities of the catalyst can be compared to peak positions and intensities of known crystalline phases that are published (in the ASTM Powder Diffraction File, for example), or that are experimentally obtained. For example, a catalyst comprised of iron oxide merely adsorbed on aluminum oxide will have an x-ray diffraction pattern of peak positions showing the distinct peak positions and intensities of iron oxide and aluminum oxide crystalline phases.

In contrast, the x-ray diffraction pattern of a solid solution catalyst containing iron shows the positions of the x-ray diffraction peaks in the solid solution catalyst to be shifted from the peak positions in the x-ray diffraction pattern of the host lattice. The shift in peak positions may be accompanied by changes in the relative intensities of the peaks, but the intensity changes are generally small.

The shift in x-ray diffraction peak positions when solid solutions are formed results from the expansion (or contraction) of the dimensions of the unit cell of the crystalline phase of the host lattice. The dimensions of the unit cell of the host lattice are changed due to the substitution of iron cations for cations of the host lattice. If the cation is larger than the cation it displaces, the unit cell dimensions will increase in size to accommodate the larger cation. The amount of expansion (or contraction if the iron cation is smaller than the host lattice cation it displaces) of the unit cell dimensions can be determined by calculating the lattice parameters of the unit cell of the solid solution phase and comparing these lattice parameters to the lattice parameters of the unit cell of the host. A change in lattice parameters due to iron substitution in a crystalline host lattice is frequently in accordance with Vegard's law (see page 221 of the above-cited reference). Since a change in the lattice parameters causes a change in the x-ray diffraction peak positions, a quick comparison of the x-ray diffraction pattern of the catalyst and the pattern of the host lattice will show whether a solid solution catalyst has been prepared.

Alternately, a more accurate method of confirming the preparation of a solid solution catalyst is to experimentally run x-ray diffraction scans of the prepared catalyst and of the host lattice and then calculate the lattice parameters of each. If the values obtained for the lattice parameters of the catalyst and host lattice are different, a solid solution catalyst has been prepared. If the geometry and dimensions (lattice parameters) of the unit cell of the host lattice is not known, it can be determined using established methods for indexing and interpreting x-ray diffraction patterns (see L. V. Azaroff and M. J. Buerger, *The Powder Method In X-Ray Crystallography*, McGraw-Hill Book Co., Inc., NY, N.Y. (1958), chapters 6 to 13). The high $2\Theta$ values (where $\Theta$ is the Bragg angle) are normally used to calculate the lattice parameters.

In the case of a solid solution catalyst stabilized with a metal oxide stabilizer, the x-ray diffraction pattern will clearly show the presence of the solid solution, which is the primary crystalline phase, and will additionally show the presence of crystalline metal oxide compounds which are present in detectable amounts. For example in the case of a solid solution catalyst of $Fe_2O_3$ in $\alpha$-$Al_2O_3$ stabilized with lanthanum, the x-ray diffraction pattern will show the presence of the $Fe_2O_3$ in $\alpha$-$Al_2O_3$ solid solution crystalline phase and crystalline compounds of lanthanum such as $La_2O_3$ and $LaAlO_3$.

In summary, the solid solution catalysts useful in this invention can be identified and characterized by (1) the presence of iron and an additional metal oxide in the catalyst, and (2) the x-ray ray diffraction pattern of the catalyst. The iron is present as cations substituted in the host lattice for cations of the host lattice. The iron content can be measured using standard analysis techniques. The x-ray diffraction pattern of the solid solution catalyst will exhibit peak positions characteristic of the host lattice but shifted due to the presence of the iron cations in the host lattice. Lattice parameters calculated for the host lattice and the solid solution catalyst will differ. The x-ray diffraction pattern of the solid solution catalysts useful in this invention will exhibit extraneous peaks in the pattern due to formation of crystalline compounds other than the solid solution catalyst itself, such as the metal oxide.

The solid solution catalysts can be prepared by first impregnating a host lattice precursor with an iron salt and a metal salt that yields the oxides upon heating, then heating the impregnated host lattice precursor to about 550° C., followed by heating to 1200° C. or more. The first heat treatment converts the salts to oxides and initiates conversion of the host lattice precursor to the host lattice. The second heat treatment completes the formation of the host lattice and produces a rearrangement of the metal atoms between the metal ions in the host lattice and the iron ions. The catalyst prepared is a solid solution catalyst containing iron, stabilized with a metal oxide stabilizer, having a distinctive x-ray diffraction pattern.

The solid solution catalyst can be prepared in other different ways. Another method is to physically admix iron oxide, metal oxide stabilizer, and the host lattice material and heat the mix to allow dissolution and substitution of the iron ions for those of the host lattice, and formation of the stabilized catalyst. Heating conditions vary for the nature of the host lattice employed, but typically are above about 1100° C.

A third method of preparation is to use the so-called sol-gel process wherein an iron salt, metal stabilizer salt, and a salt precursor of the host lattice are mixed together as solutions and a base is added to co-precipitate out a mixture of the corresponding hydrated oxides. For example, ferric nitrate, lanthanum nitrate, and aluminum nitrate can be dissolved in water and ammonium hydroxide added to the solution to coprecipitate a mixture of hydrated iron, lanthanum, and aluminum oxides. The mix is then heated to above about 1100° C. to effect dissolution and substitution of the iron ions for aluminum ions.

A fourth method is to dissolve a metal stabilizer salt in a solvent such as water or ethanol and use the solution to impregnate a preformed solid solution catalyst then dry and heat the mix to cause the metal salt to decompose upon heating to yield the oxide.

In all of these methods, an oxide precursor can be used in place of the oxide per se. The precursor, which is typically an inorganic or organic salt, decomposes on heating to yield the oxide. Examples of iron oxide precursors are iron chloride, iron sulfate, iron formate, iron oxalate, iron citrate, iron nitrate, and the like. Precursors of the oxides of metal oxide stabilizers can also be employed. Examples of lanthanum oxide precursors are lanthanum nitrate, lanthanum chloride, lanthanum sulfate, lanthanum oxalate, and the like. Likewise, the precursors of the other metal oxides are the nitrates, chlorides, sulfates, oxalates, and the like.

The solid solution catalysts useful in this invention can be used in the process in the form of a fixed bed, a fluidized bed, on a fixed support, on a fluidized support, or in any way which allows contact with the reactant.

The exiting reaction products of the oxydehydrogenation of ethane in the presence of water and the solid solution catalyst at the effective reaction temperature will be a mixture of ethylene, carbon monoxide, carbon dioxide, hydrogen chloride, residual ethane and vinyl chloride. This oxydehydrogenation process can yield less than 6%, preferably less than 4%, more preferably less than 3%, and most preferably less than 2% of vinyl chloride, and greater than 80%, preferably greater than 85%, and more preferably greater than 90% of ethylene at an ethane conversion of greater than 75%, preferably greater than 80%, more preferably greater than 85%, and most preferably greater than 90%.

The carbon monoxide and carbon dioxide are removed and the remaining products can be fed directly to an oxychlorination reaction site to prepare ethylene dichloride. Additional ethylene, oxygen and hydrogen chloride can be introduced as reactants to provide the proper reactant amounts to yield the ethylene dichloride. The exiting reaction products of the oxydehydrogenation reaction and any additional reactants for the oxychlorination reaction are contacted in the presence of a suitable catalyst at an effective reaction temperature. Suitable oxychlorination catalysts are transition metal chlorides, oxychlorides and oxides supported on a suitable carrier or the solid solution catalysts used in the oxydehydrogenation reaction. Examples of such catalysts include cupric chloride on $Al_2O_3$, $CuCl_2/KCl/Al_2O_3$, $CuCl_2/CeCl_3$, or $CuCl_2/SiAl_2O_3$. The effective reaction temperature typically ranges from about 200° C. to about 250° C. The exiting reaction products of this oxychlorination process will include ethylene dichloride, a trace amount of ethylene, a trace amount of hydrogen chloride, residual ethane and trichloroethane. The ethane can be recycled to a subsequent oxydehydrogenation reaction and the trichloroethane is removed and disposed of. The source of the trichloroethane is the vinyl chloride produced in the oxychlorination and oxydehydrochlorination steps. Since the oxydehydrogenation in the presence of water step yields a reduced amount of vinyl chloride, the amount of trichloroethane formed in oxychlorination and the costs of removal and disposal are significantly decreased.

The ethylene dichloride formed in this oxychlorination step can be processed to vinyl chloride monomer in a dehydrohalogenation process. One effective method is by pyrolysis. Suitable temperatures range from about 500° C. to about 650° C. The resultant monomer is then recovered.

By performing the oxydehydrogenation of ethane in presence of the solid solution catalyst and water, a direct feed process to vinyl chloride monomer that yields a relatively small amount of vinyl chloride monomer and trichloroethane is provided.

The following examples illustrate the concept of the invention but do not limit its scope.

EXAMPLES

Different amounts of ethane, hydrogen chloride, oxygen and water are contacted in the presence of different types of solid solution catalysts. All reactions are performed at 550° C. at a contact time of 12 seconds. The reactant amounts, catalyst types, yields of ethylene and vinyl chloride and the ethane conversion are listed in Table I.

TABLE I

| SAMPLE NO. | CATALYST TYPE[4] | $HCl/$[1] $C_2H_6$ | $O_2/$ $C_2H_6$ | $H_2O/$ $C_2H_6$ | $C_2H_6$[2] CONVERSION | YIELD[3] $C_2H_4$ | VCl |
|---|---|---|---|---|---|---|---|
| 1 | A | 1.5 | 0.7 | 2.5 | 87.4% | 83.8% | 3.0% |
| 2 | A | 1.7 | 0.8 | 1.1 | 96.0% | 78.4% | 6.0% |

TABLE I-continued

| SAMPLE NO. | CATALYST TYPE[4] | HCl/[1] $C_2H_6$ | $O_2/$ $C_2H_6$ | $H_2O/$ $C_2H_6$ | $C_2H_6$[2] CONVERSION | YIELD[3] $C_2H_4$ | VCl |
|---|---|---|---|---|---|---|---|
| 3 | A | 1.7 | 0.8 | 2.6 | 94.6% | 80.7% | 4.5% |
| 4 | B | 1.75 | 0.7 | 2.8 | 95.4% | 82.9% | 4.0% |
| 5 | C | 1.45 | 0.59 | 2.6 | 81.9% | 85.9% | 1.65% |
| 6 | C | 1.45 | 0.59 | 1.0 | 84.3% | 87.1% | 1.98% |
| 7 | C | 1.45 | 0.65 | 2.6 | 85.9% | 84.1% | 2.1% |
| 8 | C | 1.45 | 0.59 | 2.6 | 83.4% | 86.3% | 1.9% |
| 9 | C | 1.45 | 0.65 | 0.89 | 89.5% | 85.5% | 2.85% |
| 10 | C | 1.45 | 0.59 | 1.0 | 87.9% | 87.5% | 1.7% |
| 11 | C | 1.45 | 0.59 | 2.6 | 85.6% | 87.1% | 1.38% |
| 12 | C | 1.45 | 0.65 | 2.6 | 89.5% | 85.3% | 1.7% |
| 13 | C | 1.45 | 0.65 | 0.89 | 92.4% | 85.7% | 2.2% |
| 14 | C | 1.75 | 0.63 | 2.7 | 88.5% | 85.5% | 2.25% |
| 15 | C | 1.75 | 0.63 | 1.12 | 89.1% | 86.9% | 2.37% |
| 16 | C | 1.75 | 0.7 | 2.7 | 91.1% | 83.8% | 2.55% |
| 17 | C | 1.75 | 0.63 | 2.7 | 88.1% | 85.3% | 2.51% |
| 18 | C | 1.75 | 0.7 | 1.75 | 92.6% | 84.1% | 3.43% |
| 19 | C | 1.75 | 0.63 | 2.7 | 90.2% | 86.4% | 1.84% |
| 20 | C | 1.75 | 0.63 | 1.12 | 90.7% | 86.2% | 2.2% |
| 21 | C | 1.75 | 0.7 | 2.7 | 93.3% | 84.5% | 2.3% |

[1]Reactant Ratio of Reactants, i.e. HCl, $O_2$ and $H_2O$, per 1 mole of ethane.
[2]Percent conversion of ethane added as a reactant.
[3]Percent of converted ethane which yielded ethylene or vinyl chloride.
[4]Catalyst Type A is 2% $Fe_2O_3$ in attrition resistant $\alpha$-$Al_2O_3$ stabilized with 4% $La_2O_3$.
Catalyst Type B is 2% $Fe_2O_3$ in attrition resistant $\alpha$-$Al_2O_3$ stabilized with 4% $La_2O_3$, 0.5% CoO and 1% MnO.
Catalyst Type C is 2% $Fe_2O_3$ in attrition resistant $\alpha$-$Al_2O_3$ stabilized with 4% $La_2O_3$, 0.5% $Cr_2O_3$, 0.5% CoO, 1% MnO, and 1.5% BaO.

This table shows the benefits of using water as a coreactant. As a comparison to the results provided by the process of this invention, in a similar reaction using the same amounts of reactants and the same type of catalyst at the same reaction conditions as in Sample 1, but without using water as a coreactant, the vinyl chloride yield is 5.6%, the yield of ethylene is 82.1%, and the conversion of ethane is 91.9%. As a further comparison to the results provided by the process of this invention, in a similar reaction using the same amounts of reactants and the same type of catalyst at the same reaction conditions as in Sample 4, but without using water as a coreactant, the yield of vinyl chloride is 5.1%, the yield of ethylene is 83.8%, and the conversion of ethane is 95.9%. In yet another comparison, in a reaction using the same amount of reactants, the same catalyst at the same reaction conditions as in Sample 17, but without using any water, the yield of vinyl chloride is 3.54%, the yield of ethylene is 85.3% and the conversion of ethane is 93.3%.

What is claimed is:

1. A process for preparing ethylene from ethane, comprising contacting a charge amount of ethane, an oxygen source, a balanced amount of a chlorine source relative to the amount of ethane, and water in the presence of a solid solution catalyst containing iron cations stabilized with a metal oxide stabilizer, at an effective temperature.

2. The process of claim 1 wherein the oxygen source is air.

3. The process of claim 2 wherein the chlorine is hydrogen chloride gas.

4. The process of claim 3 wherein the catalyst is $Fe_2O_3$ in $\alpha$-$Al_2O_3$ stabilized with $La_2O_3$.

5. The process of claim 4 wherein the temperature ranges from between about 400° C. to about 650° C.

6. The process of claim 5 wherein the temperature ranges from about 475° C. to about 600° C.

7. The process of claim 6 wherein between about 0.7 to about 1.8 moles of hydrogen chloride, between about 0.35 to about 0.7 mole of oxygen, and between about 0.5 to about 3.0 moles of water per mole of ethane are employed.

8. The process of claim 1 wherein less than about 6% of vinyl chloride and greater than about 75% of ethylene are formed as reaction products at an ethane conversion of greater than about 80%.

9. The process of claim 8 wherein the reaction product comprises less than about 4% of vinyl chloride and greater than 80% of ethylene at an ethane conversion of greater than about 80%.

10. The process of claim 9 wherein the reaction product comprises less than about 3% of vinyl chloride and greater than 85% of ethylene at an ethane conversion of greater than 85%.

11. The process of claim 7 wherein less than about 6% of vinyl chloride and greater than about 75% of ethylene are formed as reaction products at an ethane conversion of greater than about 80%.

12. The process of claim 11 wherein the reaction product comprises less than about 4% of vinyl chloride and greater than 80% of ethylene at an ethane conversion of greater than about 80%.

13. The process of claim 12 wherein the reaction comprises less than about 3% of vinyl chloride and greater than 85% of ethylene at an ethane conversion of greater than 85%.

* * * * *